(12) United States Patent
Niedermeier

(10) Patent No.: US 8,324,577 B2
(45) Date of Patent: Dec. 4, 2012

(54) METHOD AND DEVICE FOR DETERMINING THE MASS AND/OR A MASS PROPORTION OF A WALL SECTION OF A PLASTIC BOTTLE

(75) Inventor: Anton Niedermeier, Offenstetten (DE)

(73) Assignee: Krones AG, Neutraubling (DE)

( * ) Notice: Subject to any disclaimer, the term of this patent is extended or adjusted under 35 U.S.C. 154(b) by 141 days.

(21) Appl. No.: 12/877,578

(22) Filed: Sep. 8, 2010

(65) Prior Publication Data

US 2011/0058156 A1    Mar. 10, 2011

(30) Foreign Application Priority Data

Sep. 8, 2009  (DE) .......................... 10 2009 040 626

(51) Int. Cl.
*G01J 1/00* (2006.01)
(52) U.S. Cl. .................................................. 250/336.1
(58) Field of Classification Search ................. 250/336.1
See application file for complete search history.

(56) References Cited

U.S. PATENT DOCUMENTS

| 5,585,603 | A | 12/1996 | Vogeley, Jr. |
| 6,620,352 | B1 * | 9/2003 | Davis et al. .................. 264/40.4 |
| 7,253,892 | B2 * | 8/2007 | Semersky et al. .......... 356/237.6 |
| 2005/0087691 | A1 | 4/2005 | Cochran et al. |
| 2008/0211125 | A1 | 9/2008 | Derrien et al. |
| 2009/0147082 | A1 | 6/2009 | Detrois et al. |

FOREIGN PATENT DOCUMENTS

DE  102005044206 A1   3/2007
WO  WO-2008027569 A2   3/2008

OTHER PUBLICATIONS

German Search Report for DE102009040626.3 dated Mar. 18, 2010.

* cited by examiner

*Primary Examiner* — Christine Sung
(74) *Attorney, Agent, or Firm* — Marshall, Gerstein & Borun LLP

(57) ABSTRACT

A method and device for the determination of the mass and/or the mass proportion of a wall section of a plastic bottle, in particular a section in the vicinity of the bottle shoulder and/or of the bottle neck, where, due to the fact that a relative mass distribution of the side wall is calculated from a distribution of the light transmission through the side wall of the bottle, the mass proportion of the wall section to be determined of the mass of the side wall can be determined with slight error based on the mass distribution even without calculation of the absolute mass values.

18 Claims, 2 Drawing Sheets

METHOD AND DEVICE FOR DETERMINING THE MASS AND/OR A MASS PROPORTION OF A WALL SECTION OF A PLASTIC BOTTLE

CROSS-REFERENCE TO RELATED APPLICATION

The present application claims the benefit of priority of German Application No. 102009040626.3, filed Sep. 8, 2009. The entire text of the priority application is incorporated herein by reference in its entirety.

FIELD OF THE DISCLOSURE

The disclosure relates to a method for the determination of the mass and/or a mass proportion of a wall section of a plastic bottle, in particular a section in the vicinity of the bottle shoulder and/or of the bottle neck, as well as a device for the use of the.

BACKGROUND

During the stretch blowing of plastic bottles, in particular PET bottles, it is desirable for reasons of quality assurance and process control to deter mine the mass or the mass proportion of individual regions of the bottles, such as for example the bottle bottom or the bottle shoulder. As is known, for this purpose bottles can be ejected from the production flow on a random sample basis and cut up in order to then weigh the sections to be inspected. However, it would be desirable to determine the mass of individual wall regions non-destructively and with less delay in the on-going product flow.

For this type of examination of the bottle bottom it is known from DE 10 2005 044 206 A2 that—in a flow of bottles to be inspected running continuously through an inspection device in neck handling—in each case light can be passed through the bottle bottom from below and, through the mouth of the bottle, the bottle bottom can be displayed in an image. According to the surface curvature of the bottle bottom, the camera image reveals here characteristic bright/dark structures, from which various quality features, in particular though the mass of the bottle bottom, can be determined non-destructively in the on-going process.

However, also the shoulder or neck region of the bottle is of particular interest, because when too little material is used in this region, the nitrogen and optionally carbon dioxide existing above the charged product can escape through the bottle wall to an unwanted extent and to the detriment of the product quality.

Indeed, it is known from WO 2008/027569 A2 that light can be passed approximately radially and aligned through the side wall of a rotationally symmetrical plastic bottle using a vertical light-emitting diode array and that the light transmission can be determined, locally dispersed, after light penetration through the bottle wall on both sides, using an appropriate number of detectors arranged one above the other. However, light is only passed through the bottle wall at points, so that the wall regions in the intervening spaces of the irradiating grid are not included. It may be however that it is just those wall sections that are not included which are particularly problematical. The irradiation grid also results in that the limits of the measurement range cannot be matched as required to the bottle shape. In addition an absolute value for the associated wall thickness must be determined from the relevant transmission through the bottle wall and in turn from this the mass of the associated wall section. This is however subject to comparatively large errors.

SUMMARY OF THE DISCLOSURE

It is therefore an aspect of the disclosure to provide a method which can determine the mass or the mass proportion of a vertical section in the shoulder or neck region for various types of bottle completely, with sufficient accuracy and non-destructively.

This aspect is provided in that the method comprises the following steps: a) irradiation of an irradiation region of the bottle side wall with light, in particular with infrared or ultraviolet light, and to acquire a light distribution of the light penetrating the bottle along a detection region of the side wall on the side of the bottle facing away from the irradiation region; b) calculation of a mass distribution of the bottle side wall from the light distribution; and c) determination of the mass proportion of the wall section to be determined of the mass of the side wall based on the mass distribution.

Through the relative measurement of the mass distribution an erroneous conversion of individual measuring points of the light distribution in absolute mass values can be avoided. From the mass distribution the mass proportions of any definable wall sections can be determined.

Preferably in step c) the mass proportion is calculated by integration of the mass distribution over the wall section and by forming a relationship with the integral of the mass distribution over the detection region. In this way standardised calculation methods can be made available for each bottle shape, so that measurement results can be compared against one another even in relative form.

Preferably the irradiation region and the detection region extend from the bottle bottom up to the mouth region of the bottle. Since the weight of the bottle bottom and of the mouth region can be determined separately, the figure for the mass proportion of the wall section to be examined is particularly meaningful.

Preferably the mass distribution states the distribution of the mass along a line essentially parallel to the principal axis of the bottle. In this way the mass distribution is particularly well suited to the determination of the mass or of the mass proportion of a fully circumferential, rotationally symmetrical wall section.

Preferably the mass distribution is calculated based on a calibration which produces a relationship between the light distribution and the mass distribution, in particular taking into consideration the contouring of the bottle. In this way the mass distribution can be particularly accurately determined.

Preferably the light distribution is measured based on a calibration which takes into account the spatial intensity distribution of the light in the irradiation region. In this way irregularities in the light source can be compensated.

Preferably the light distribution is acquired in at least one camera image. This facilitates a simultaneous visual inspection of the bottle and uncritical data acquisition with regard to the sideward bottle position.

Preferably the detection region is reproduced in a camera image and determined by the selection of pixels in the camera image. This facilitates particularly flexible adaptation of the evaluation to various bottle shapes.

Preferably the irradiation region is orientated essentially strip-shaped and parallel to the principal axis of the bottle. In this way unwanted reflected glare and light refraction on the bottle can be limited.

Preferably the bottle is held at the mouth region off-floor during the irradiation. A determination of the bottom weight during illumination of the bottom can then take place directly before or after the determination of the mass distribution.

Preferably the bottle is irradiated with pulsed light. This facilitates a particularly accurate triggering of the irradiation and detection in the on-going production flow.

A particularly favourable embodiment comprises furthermore the following steps in the method: d) calculation of the mass of the bottle side wall from the difference of the known total mass of the bottle and the known mass of the bottle bottom and of the mouth region; and e) determination of the mass of the wall section from the mass proportion of the wall section and the mass of the side wall. In this way the absolute mass of the wall section to be examined can be determined accurately in a simple manner.

Preferably the bottle is a bottle manufactured using the blowing or stretch blowing method, whereby the total mass of the bottle essentially corresponds to the mass of the bottle preform used and the mouth region of the bottle during blowing or stretch blowing is not distorted so that the total mass and the mass of the mouth region each enter the calculation in step a) as constants. In this way unvarying sections of the bottle can be determined beforehand by random sample weighing with high precision.

The technical aspect is also solved with a device for implementation of the method according to the disclosure, which comprises: a light source for irradiating the irradiation region; a detector for acquiring the light distribution along the detection region; an evaluation unit for calculating the mass and/or the mass proportion of the wall section to be inspected. The device according to the invention can determine the mass or the mass proportion of the wall section to be inspected with high accuracy.

Preferably the device comprises a means of transport, which feeds a continuous flow of bottles to be examined off-floor between the light source and the detector. Thus the device can be particularly effectively coupled with a device for the determination of the mass of the bottle bottom.

BRIEF DESCRIPTION OF THE DRAWINGS

An embodiment of the disclosure is illustrated in the drawing. The following are shown.

DETAILED DESCRIPTION OF THE PREFERRED EMBODIMENT

Figure 1:
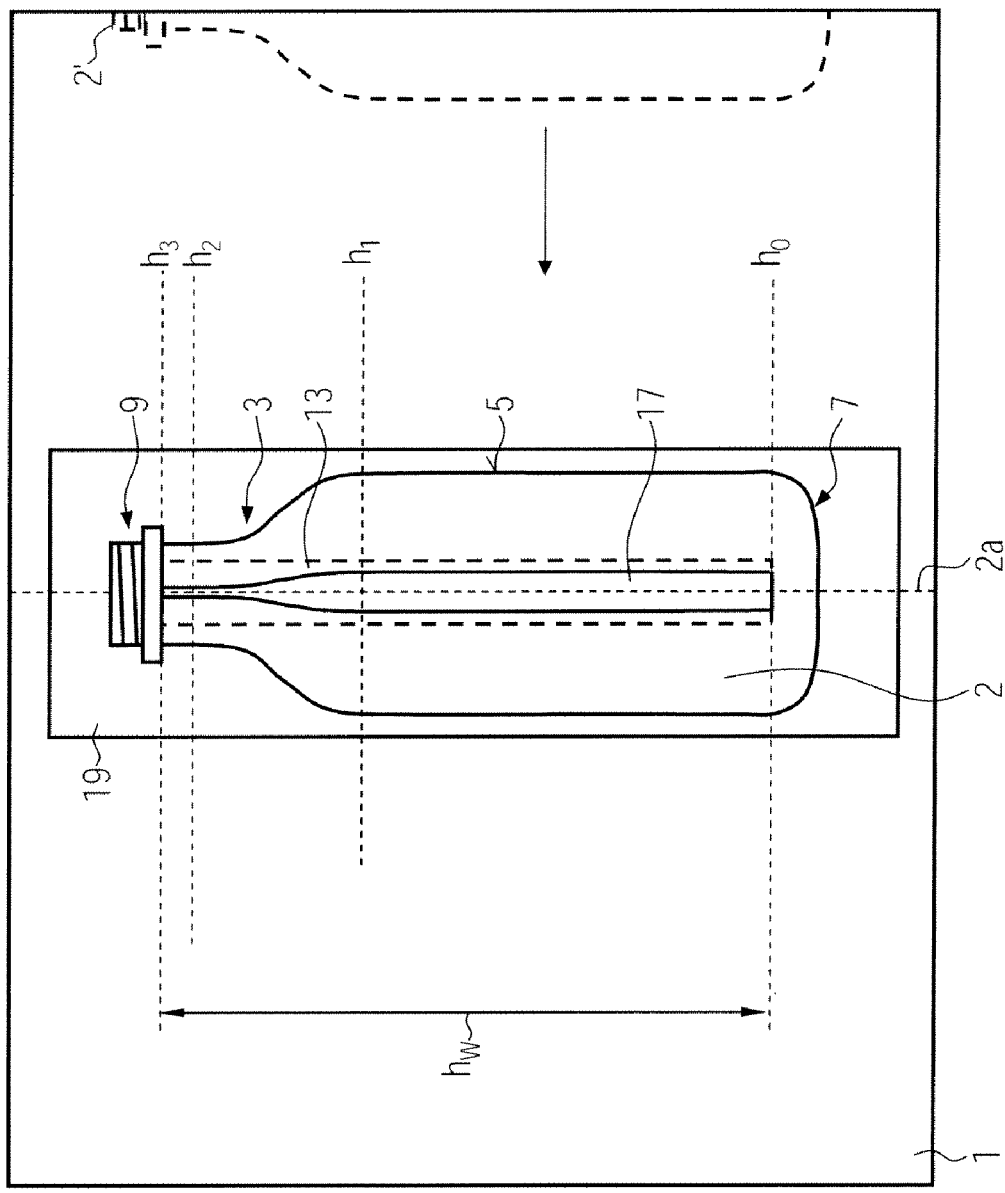
FIG. 1 a camera image of a bottle through which light is passed.

FIG. 1 illustrates a camera image 1 of an essentially rotationally symmetrical bottle 2 to be examined with a fully circumferential wall section 3, which in particular can correspond to the region of the bottle shoulder and/or bottle neck, the mass $m_S$ of which or the mass proportion $\omega_S$ of which on the bottle wall 5 is to be determined. The wall section 3 is a section of the sideward bottle wall 5, which extends between the bottle bottom 7 and the mouth region 9 of the bottle 2.

Figure 2:
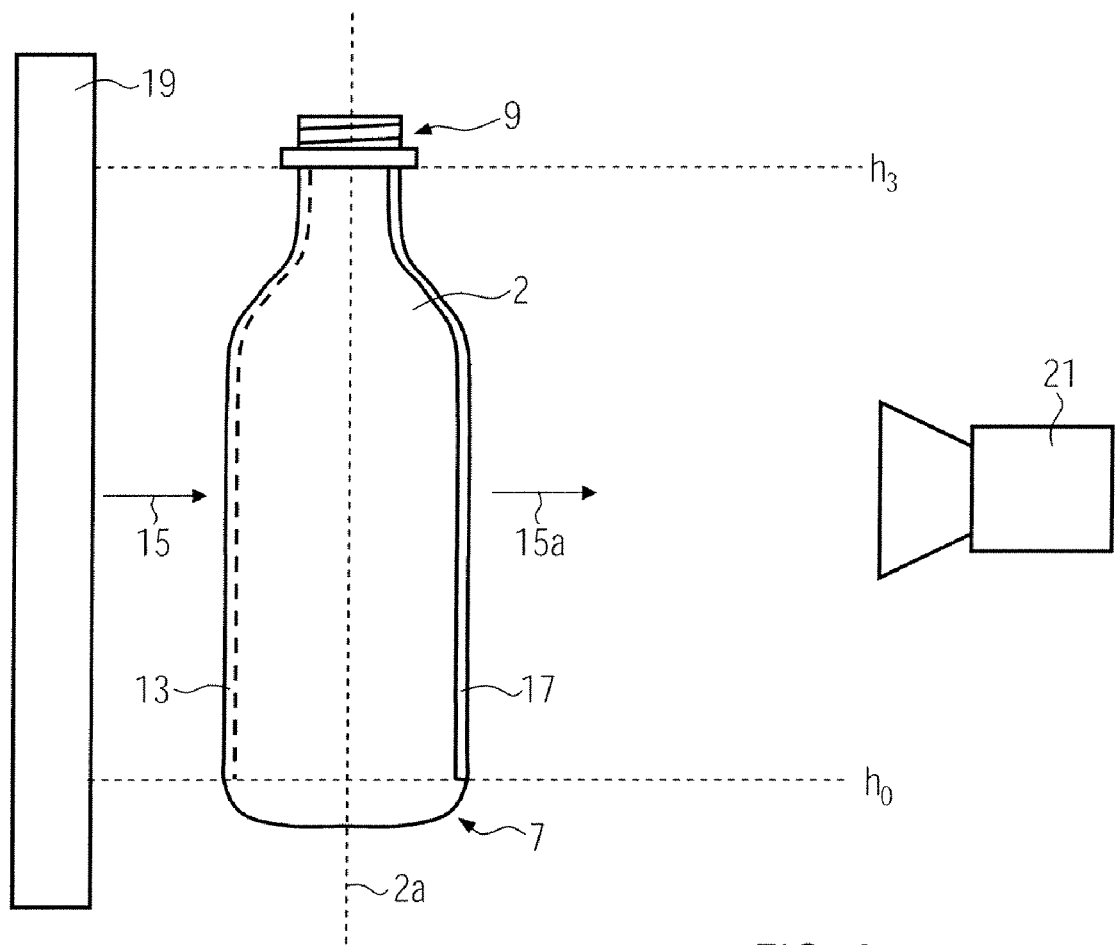
FIG. 2 a schematic partial view of a measurement device for implementation of the method according to the disclosure.
Figure 3:
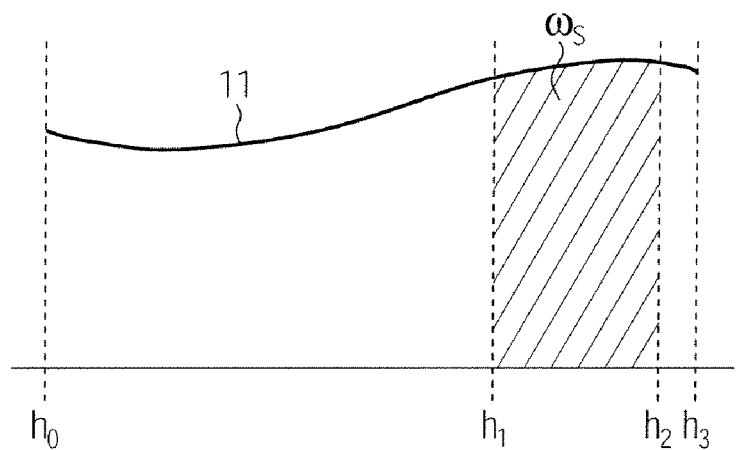
FIG. 3 a mass distribution of the side wall.

As FIGS. 2 and 3 also clearly show, the disclosure relates to the determination of a relative mass distribution 11 of the bottle wall 5, in particular between the bottom 7 and the mouth region 9. For this purpose, an irradiation region 13 of the bottle wall 5 is firstly irradiated at the side with light 15, in particular with infrared or ultraviolet light, and the distribution 16 (not illustrated) of the light proportion 15a penetrating the bottle wall 5 in an oppositely situated detection region 17 is measured.

Then from the distribution 16 of the light transmission 15a the mass distribution 11 is calculated, preferably with the inclusion of a calibration based on comparative data obtained beforehand, which produces a direct relationship between the light transmission 15a through a certain section of the bottle wall 5 and its mass or mass proportion of the bottle wall 5. In this connection it is expedient to separately calibrate each type of bottle to be examined, so that the influence of the bottle shape on the measured light distribution 16, for example due to light reflection and/or light refraction, or on the calculated mass distribution 11 is considered.

It is sufficient to determine the mass distribution 11 in relative form. Consequently, the measurements of the radiation transmission 15a, for example grey scales of individual pixels, do not need to be converted into an absolute mass individually.

In the following an embodiment of the disclosure for the determination of the (absolute) mass $m_S$ of the wall section 3 is described. However, it may be sufficient to only determine its (relative) mass proportion $\omega_S$ which is defined in the following. Then the steps in the method for the determination of the relevant (absolute) masses do not need to be carried out.

The total mass $m_T$ of the bottle 2 manufactured in the blowing or stretch blowing method corresponds to that of the bottle preform used (not shown) and can therefore be determined by weighing it on a random sample basis. Furthermore, the mass $m_M$ of the mouth region 9, which normally does not deform during stretch blowing, can be determined beforehand by parting and separate weighing of the mouth region 9. The masses $m_T$ and $m_M$ can thus be assumed as known for the implementation of the method according to the disclosure and are each used in the method as a constant which is characteristic of a certain type of bottle.

The mass $m_B$ of the bottle bottom can be determined separately for each bottle in the entering or exiting product flow, for example with the method known from DE 10 2005 044 206 A2, and can thus also be assumed as known in the implementation of the method according to the disclosure. The mass $m_B$ is used in the method as a characteristic constant for each single bottle.

The mass $m_W$ of the bottle wall 5 between the bottom 7 and the mouth region 9 can therefore be determined as follows:

$$m_W = m_T - (m_M + m_B).$$

In the embodiment the relative mass distribution 11, which is schematically illustrated in FIG. 3, is determined between the bottom 7 and the mouth region 9, whereby the integral of the mass distribution 11 over the total height $h_w$ (from $h_0$ to $h_3$) of the bottle wall 5 corresponds to the mass $m_W$ of the bottle wall 5 or a mass proportion $\omega_W$ equal to 1. If the wall section 3 to be examined is defined as a region between a lower vertical position $h_1$ and an upper vertical position $h_2$, then the integral of the mass distribution 11 from $h_1$ to $h_2$ gives the mass proportion $\omega_S$ of the region 3 of the bottle wall 5 to be examined, represented in FIG. 3 as the shaded area under the mass distribution 11. The absolute mass $m_S$ of the region 3 to be examined is given then as follows:

$$m_S = m_W * \omega_S / \omega_W.$$

In this connection the wall section 3 can be any region of the bottle wall 5, for example up to the mouth region 9.

The advantage of this method is on one hand that the absolute mass $m_W$ of the bottle wall 5 can be determined simply and accurately and is included in the method as a constant. On the other hand, the mass distribution 11 can be determined in relative form and an erroneous conversion of individual transmission values into absolute mass values is avoided.

FIGS. 1 and 2 clearly show a suitable irradiation arrangement for implementing the method. According to this, the irradiation region 13 extends between the bottle bottom 7 and the mouth region 9 on a first side of the bottle 2 facing a light source 19 and the detection region 17 on the oppositely situated side facing a preferably image-generating light detector 21. This means that the light entry or exit on the bottle wall 5 preferably occurs in each case over the complete height $h_w$.

The width of the irradiation region 13 and/or of the detection region 17 or its projection in the camera image 1 can be adapted as required. For example, the irradiation region 13, the outline of which is indicated as a broken line in FIGS. 1 and 2, can be strip-shaped. The bottle 2 could however also be irradiated on half a side.

The bottle 2 is passed off-floor in neck handling as part of a continuous product flow, for example by a rotating means of transport (not illustrated), between the light source 19 and the detector 21 in order to facilitate an unrestricted preceding or subsequent inspection of the bottle bottom 7.

The light source 19 preferably emits pulsed light 15, which is so strongly absorbed by the bottle wall 5 that different layer thicknesses or masses of the bottle wall 5 produce measurement signals at the detector 21 which can be differentiated from one another. The light 15 is preferably located within a defined spectral range, preferably in the infrared, in particular in the spectral range of 1.6 to 5 μm or in the ultraviolet, especially in the spectral range from 300 to 320 nm. However, principally any electromagnetic radiation can be used which is absorbed in the bottle wall 5 to a suitable extent, such as for example soft X-rays.

The light source 19 can be formed as a large-area radiator, in particular as a light screen with light-emitting diodes which is at least as high as the bottle wall 5, so that the radiated light 15 covers the bottle wall 5 between the bottom 7 and the mouth region 9 at least in a circumferential partial region. The beam path on the irradiated side can be made appropriately long for the most possible aligned irradiation of the bottle wall 5. Similarly it is possible to mask out divergent parts of the beam by slit screens in the irradiated side of the beam path. The principal beam direction of the light source 19 is preferably perpendicular to the principal axis 2a of the bottle.

An aligned irradiation is desirable to guide the largest possible proportion of the radiation through the bottle 2 at small entry and exit angles in order to minimise reflections and refraction at the surfaces of the bottle wall 5. However, it may also be advantageous depending on the application, to irradiate the bottle wall 5 diffusely.

The intensity distribution of the light 15 incident in the irradiation region 13 is as homogeneous as possible. For this purpose the radiation pattern of the light source 19 can be specially adapted. It is however in any case advantageous to determine the spatial brightness distribution of the incident light 15 in the irradiation region 13 using an irradiation calibration and to take it into account when calculating the mass distribution 11.

The detector 21 is preferably a camera. The width of the detection region 17 can be specified by allotting a suitable region or the associated pixels in the camera image 1 as required. As indicated in FIG. 1, sideward delimitation lines of the detection region 17 could approximately follow the bottle shape, so that in each case a uniform in circumferential region of the bottle wall 5 is acquired. The width or the sideward delimitation lines of the detection region 17 could however also be adapted to special surface structures such as recessed grips, beading, etc. Also the position of the wall section 3 to be examined, i.e. the heights $h_1$ and $h_2$, could be set comfortably in the camera image 1 and inspected. It is however also conceivable that the detector 21 is just formed as a linear detector array.

Preferably the light distribution 16 is acquired along a line essentially parallel to the principal axis 2a of the bottle 2 or the mass distribution 11 is calculated in a suitable orientation. This simplifies the evaluation with essentially rotationally symmetrical bottles. Depending on the bottle shape the detection region 17 can also however follow a line adapted to asymmetrical structures or the calculation of the mass distribution 11 can be appropriately adapted.

For the most possibly aligned detection the beam path on the detection side can be made appropriately long, for example by using a camera lens with a long focal length.

Since the bottle 2 moves continuously in a product flow during the inspection, as indicated in FIG. 1 by another bottle 2' illustrated with a broken line and the associated arrow, the time point of illumination, for example in the form of a flash of light, and/or the time point of detection or image exposure, is co-ordinated with the bottle movement. A control unit (not illustrated) is provided for this purpose. Furthermore, an evaluation unit (not illustrated) for evaluating the light transmission and calculating the mass $m_S$ and/or the mass proportion $\omega_S$ is provided.

The invention claimed is:

1. Method of determining the mass ($m_S$) and/or a mass proportion ($\omega_S$) of a wall section of a plastic bottle, comprising:
   a) irradiating an irradiation region of a bottle side wall with light, acquiring a light distribution of the light penetrating the bottle along a detection region of the side wall on the side of the bottle facing away from the irradiation region, and distinguishing measurement signals of the light distribution, the measurement signals produced by the irradiated light being absorbed by different layer thicknesses or masses of the bottle sidewall;
   b) calculating a mass distribution of the bottle side wall from the light distribution; and
   c) determining the mass proportion ($\omega_S$) of the mass ($m_W$) of the side wall (5) based on the mass distribution (11).

2. Method according to claim 1, wherein in step c) calculating the mass proportion ($\omega_S$) by integration of the mass distribution over the wall section and by forming a relationship with the integral of the mass distribution over the detection area.

3. Method according to claim 1, and extending the irradiation region and the detection region from a bottle bottom to a mouth region of the bottle.

4. Method according to claim 1, wherein the mass distribution states the distribution of the mass along a line essentially parallel to a principal axis of the bottle.

5. Method according to claim 1, and calculating the mass distribution based on a calibration which produces a relationship between the light distribution and the mass distribution.

6. Method according to claim 5, and taking into consideration a contouring of the bottle.

7. Method according to claim 1, and measuring the light distribution based on a calibration which takes into account a spatial intensity distribution of the light in the irradiation region.

8. Method according to claim 1, and acquiring the light distribution in at least one camera image.

9. Method according to claim 1, and reproducing the detection region in a camera image and then determining the detection region by a selection of pixels in the camera image.

10. Method according to claim 1, wherein the irradiation region is essentially strip-shaped and orientated parallel to a principal axis of the bottle.

11. Method according to claim 1, and holding the bottle off-floor at a mouth region during the irradiation.

12. Method according to claim 1, and irradiating the bottle with pulsed light.

13. Method according to claim 1, and further comprising:
   d) calculating the mass ($m_W$) of the bottle side wall from the difference between a known total mass ($m_T$) of the bottle and known masses ($m_B$, $m_M$) of a bottle bottom and of a mouth region of the bottle; and
   e) determining the mass ($m_S$) of the wall section from the mass proportion ($\omega_S$) of the wall section and the mass ($m_S$) of the side wall.

14. Method according to claim 1, wherein the bottle is a bottle manufactured using a blowing or stretch blowing method, and wherein a total mass ($m_T$) of the bottle essentially corresponds to a mass of the bottle preform used and a mouth region of the bottle during blowing or stretch blowing is not distorted so that a total mass ($m_T$) and a mass ($m_M$) of the mouth region each enter the calculation in step a) as constants.

15. Method according to claim 1, wherein irradiating with light comprises with infrared or ultraviolet light.

16. Method according to claim 1, wherein the wall section of the plastic bottle is a section in the region of a bottle shoulder and/or of a bottle neck.

17. Device for determining a mass ($m_S$) and/or a mass proportion ($\omega_S$) of a wall section of a plastic bottle, the device comprising:
   a light source for irradiating an irradiation region of a bottle side wall with light;
   a detector for the acquisition of a light distribution of the light penetrating the bottle along a detection region of the side wall on the side of the bottle facing away from the irradiation region;
   an evaluation unit for calculating a mass distribution of the bottle side wall from the light distribution; and
   an evaluation unit for determining the mass proportion ($\omega_s$) of the mass ($m_s$) of the side wall (5) based in the mass distribution (11), the evaluation unit including logic for:
   distinguishing measurement signals of the light distribution, the measurement signals produced by the irradiated light being absorbed by different layer thicknesses or masses of the bottle sidewall.

18. Device according to claim 17, and a means of transport, which feeds a continuous flow of bottles to be examined off-floor between the light source and the detector.

* * * * *